(12) United States Patent
Bunn et al.

(10) Patent No.: US 12,144,648 B2
(45) Date of Patent: Nov. 19, 2024

(54) INFANT MONITORING DEVICE

(71) Applicant: Owlet Baby Care, Inc., Lehi, UT (US)

(72) Inventors: Michael Bunn, Lehi, UT (US); Taylor Hooker, Lehi, UT (US); Seth Munger, Springville, UT (US)

(73) Assignee: OWLET BABY CARE, INC., Lehi, UT (US)

( * ) Notice: Subject to any disclaimer, the term of this patent is extended or adjusted under 35 U.S.C. 154(b) by 432 days.

(21) Appl. No.: 17/352,081

(22) Filed: Jun. 18, 2021

(65) Prior Publication Data

US 2021/0393200 A1 Dec. 23, 2021

Related U.S. Application Data

(60) Provisional application No. 63/042,203, filed on Jun. 22, 2020, provisional application No. 63/042,511, filed on Jun. 22, 2020.

(51) Int. Cl.
*A61B 5/00* (2006.01)
*A61B 5/01* (2006.01)
(Continued)

(52) U.S. Cl.
CPC .......... *A61B 5/6807* (2013.01); *A61B 5/0059* (2013.01); *A61B 5/01* (2013.01); *A61B 5/14551* (2013.01); *A61B 5/6831* (2013.01); *A61B 5/7221* (2013.01); *A61B 5/02438* (2013.01); *A61B 2503/04* (2013.01); *A61B 2560/0214* (2013.01); *A61B 2560/0252* (2013.01);
(Continued)

(58) Field of Classification Search
None
See application file for complete search history.

(56) References Cited

U.S. PATENT DOCUMENTS

| 4,228,548 A | 10/1980 | Cohen |
| 4,778,452 A | 10/1988 | Moden et al. |

(Continued)

FOREIGN PATENT DOCUMENTS

| CN | 303928185 | 11/2016 |
| JP | 2008194323 A | 8/2008 |

(Continued)

OTHER PUBLICATIONS

Jordan Crook, Owlet Infant Health Tracker Takes The Wearable Revolution Into The Crib, https://techcrunch.com/2014/01/08/owlet-infant-health-tracker-takes-the-wearable-revolution-into-the-crib/, Jan. 8, 2014, viewed on Oct. 6, 2023.*

(Continued)

*Primary Examiner* — Catherine M Voorhees
*Assistant Examiner* — James Moss
(74) *Attorney, Agent, or Firm* — Workman Nydegger

(57) ABSTRACT

An infant monitoring device is disclosed having a band or sock configured to wrap around the foot or other portion of an infant. The sock houses a removable sensing module configured to couple to the sock and measure health parameters of the infant. The sensing module is removably couplable with a base station that charges the sensing module. The sensing module transmits and receives information from the base station. Both the base station and the sensing module can transmit and receive information from a remote location.

14 Claims, 16 Drawing Sheets

(51) Int. Cl.
*A61B 5/1455* (2006.01)
*A61B 5/024* (2006.01)
(52) U.S. Cl.
CPC ............. *A61B 2560/0443* (2013.01); *A61B 2562/0271* (2013.01)

(56) References Cited

U.S. PATENT DOCUMENTS

| | | | |
|---|---|---|---|
| 5,385,537 | A | 1/1995 | Davini |
| D541,684 | S | 5/2007 | Sandy et al. |
| D569,985 | S | 5/2008 | Ganapathy et al. |
| D585,605 | S | 1/2009 | Kamradt |
| D604,856 | S | 11/2009 | Arbesman et al. |
| 7,713,223 | B2 | 5/2010 | Weber et al. |
| 7,887,492 | B1 | 2/2011 | Rulkov et al. |
| D649,718 | S | 11/2011 | Baum et al. |
| D665,539 | S | 8/2012 | Manalo et al. |
| D681,831 | S | 5/2013 | Samlaska |
| D706,429 | S | 6/2014 | Julian et al. |
| 8,814,792 | B2 | 8/2014 | Raptis et al. |
| D719,267 | S | 12/2014 | Vaccarella |
| 8,922,788 | B2 | 12/2014 | Addison et al. |
| D730,761 | S | 6/2015 | Spaeth et al. |
| D738,514 | S | 9/2015 | Tagami et al. |
| D746,161 | S | 12/2015 | Vardi |
| D762,331 | S | 7/2016 | Dixon |
| 9,642,538 | B2 | 5/2017 | Newberry |
| 9,662,053 | B2 | 5/2017 | Richards et al. |
| 9,693,730 | B2 | 7/2017 | Workman et al. |
| D798,170 | S | 9/2017 | Toth et al. |
| D812,501 | S | 3/2018 | Kuh et al. |
| D815,289 | S | 4/2018 | Evers et al. |
| D821,571 | S | 6/2018 | Stonecipher et al. |
| D822,717 | S | 7/2018 | Lim |
| D823,466 | S | 7/2018 | Marogil |
| D826,396 | S | 8/2018 | Stonecipher et al. |
| D827,144 | S | 8/2018 | Oliveira et al. |
| D829,889 | S | 10/2018 | Hwang et al. |
| D830,537 | S | 10/2018 | Hwang et al. |
| D836,472 | S | 12/2018 | Zhiyuan |
| D838,372 | S | 1/2019 | Goering et al. |
| D840,024 | S | 2/2019 | Stonecipher et al. |
| D842,715 | S | 3/2019 | Fleet |
| D842,996 | S | 3/2019 | Frick et al. |
| 10,219,709 | B2 | 3/2019 | Basu |
| D852,965 | S | 7/2019 | Bahney et al. |
| D855,040 | S | 7/2019 | Fu et al. |
| D855,191 | S | 7/2019 | Hong et al. |
| D856,953 | S | 8/2019 | Chen et al. |
| 10,406,345 | B2 | 9/2019 | Silver et al. |
| 10,420,470 | B2 | 9/2019 | Kwon et al. |
| 10,499,837 | B2 | 12/2019 | Workman et al. |
| D873,420 | S | 1/2020 | Hinshon |
| 10,537,270 | B2 | 1/2020 | Sarussi et al. |
| 10,542,894 | B2 | 1/2020 | Zhao et al. |
| D874,399 | S | 2/2020 | Lockenwitz |
| D877,344 | S | 3/2020 | Munger |
| D877,892 | S | 3/2020 | Stonecipher et al. |
| D878,550 | S | 3/2020 | Stonecipher et al. |
| D881,388 | S | 4/2020 | Ziemann et al. |
| D893,034 | S | 8/2020 | Kase et al. |
| D895,124 | S | 9/2020 | Wielunski et al. |
| 10,835,406 | B2 | 11/2020 | Erwin et al. |
| D914,218 | S | 3/2021 | Govari et al. |
| 10,973,495 | B2 | 4/2021 | Vardi et al. |
| D919,103 | S | 5/2021 | MacPherson et al. |
| D919,821 | S | 5/2021 | Fosler et al. |
| D926,325 | S | 7/2021 | Barry et al. |
| D928,704 | S | 8/2021 | Ebrahimi Afrouzi et al. |
| 11,079,225 | B2 | 8/2021 | Ong et al. |
| 11,083,371 | B1 | 8/2021 | Szabados et al. |
| D934,191 | S | 10/2021 | Lv et al. |
| D940,881 | S | 1/2022 | Hadley et al. |
| D946,766 | S | 3/2022 | Bunn et al. |
| 2002/0133067 | A1* | 9/2002 | Jackson, III ......... A61B 5/6829 600/323 |
| 2004/0133081 | A1* | 7/2004 | Teller .................. A61B 5/4884 600/595 |
| 2005/0228244 | A1 | 10/2005 | Banet |
| 2007/0073129 | A1 | 3/2007 | Shah et al. |
| 2010/0234706 | A1* | 9/2010 | Gilland ............. A61B 5/14552 600/344 |
| 2010/0317938 | A1 | 12/2010 | Kuhn et al. |
| 2012/0130210 | A1 | 5/2012 | Kall |
| 2013/0030259 | A1 | 1/2013 | Thomsen et al. |
| 2015/0201846 | A1* | 7/2015 | Maiershon ............. G16H 40/67 600/301 |
| 2015/0216454 | A1 | 8/2015 | Kasahara et al. |
| 2015/0342527 | A1 | 12/2015 | Karnik et al. |
| 2016/0058380 | A1 | 3/2016 | Lee et al. |
| 2016/0192856 | A1* | 7/2016 | Lee ...................... A61B 5/0006 600/382 |
| 2017/0014040 | A1 | 1/2017 | Shim et al. |
| 2017/0245791 | A1* | 8/2017 | Workman .......... A61B 5/14551 |
| 2017/0315511 | A1 | 11/2017 | Shim et al. |
| 2018/0317785 | A1 | 11/2018 | MacDonald et al. |
| 2019/0008432 | A1 | 1/2019 | Bashan et al. |
| 2019/0028662 | A1 | 1/2019 | Kulcke et al. |
| 2019/0150527 | A1 | 5/2019 | Oleson et al. |
| 2019/0209060 | A1 | 7/2019 | Katra |
| 2019/0223806 | A1 | 7/2019 | Bennet et al. |
| 2019/0298175 | A1 | 10/2019 | Matsui et al. |
| 2020/0015690 | A1 | 1/2020 | Choi et al. |
| 2020/0044466 | A1* | 2/2020 | Piercey ................. H02J 7/0042 |
| 2020/0060590 | A1 | 2/2020 | Workman et al. |
| 2021/0193977 | A1 | 6/2021 | Reykhert |
| 2021/0393202 | A1 | 12/2021 | Jones et al. |

FOREIGN PATENT DOCUMENTS

| | | |
|---|---|---|
| WO | WO 9004352 A1 | 5/1990 |
| WO | WO 2016178986 A1 | 11/2016 |
| WO | WO 2019175122 A2 | 9/2019 |
| WO | WO 2019181268 A1 | 9/2019 |
| WO | WO 2019214990 A1 | 11/2019 |
| WO | WO 2019226692 A1 | 11/2019 |
| WO | WO 2021262552 A1 | 12/2021 |

OTHER PUBLICATIONS

Alharbi et al.; "Oxygen Saturation Measurements from Green and Orange Illuminations of Multi-Wavelength Optoelectronic Patch Sensors;" Sensors; (2019); 17 pages; vol. 19, No. 118; <doi:10.3390/s19010118>.

BSX Technologies; "Red Light versus Green Light: The Future of Optical Sensing in Wearable Devices;" bsxtechnologies [online]; (Aug. 16, 2016); 5 pages; [Retrieved Feb. 20, 2022]; retrieved from <URL: https://medium.com/bsxtechnologies/red-light-versus-green-light-74fdd5fe7027 >.

Castaneda et al.; "A Review on Wearable Photoplethysmography Sensors and their Potential Future Applications in Health Care;" International Journal of Biosensors & Bioelectronics; [Author Manuscript]; (2018); pp. 195-202; vol. 4, No. 4; <doi: 10.15406/jibsbe.2018.04.00125 >.

Chang et al.; "MW-PPG Sensor: An on-Chip Spectrometer Approach;" Sensors; (2019); 16 pages; vol. 19, No. 3698; <doi: 10.3390/s19173698 >.

Dolan; "Owlet Stops Selling Sleep Sock after Receiving Warning from the FDA;" Gray News; [online]; (Dec. 2, 2021); 7 pages; [Retrieved on Jun. 1, 2022]; retrieved from <URL: https://www.whsv.com/2021/12/02/owlet-stops-selling-sleep-sock-after-receiving-warning-fda/#:-:text=The%20company%20plans%20to%20offer.U.S.%20sometime%20in%20January%202022 >.

EDN; "LED-based Sensors for Wearable Fitness Tracking Products;" EDN.com; (Dec. 16, 2014); 9 pages; Retrieved from <URL: edn.com/led-based-sensors-for-wearable-fitness-tracking-products/ >.

Mcgrane; "Cardiac Insight Raises $4.5M, Wins FDA Approval to Launch Wearable ECG Sensor;" GeekWire; (Apr. 20, 2017); 8

(56) References Cited

OTHER PUBLICATIONS pages; [retrieved on Jun. 1, 2022]; retrieved from <URL: https://www/geekwire.com/2017/cardiac-insight-raises-2-m-launches-wearable-ecg-sensor/>.

Owlet Smart Sock 3 Unboxing; "Best Baby Monitor 2021;" Sandra B. [YouTube]; (Sep. 21, 2020); 1 page; [Retrieved on Nov. 2, 2021]; retrieved from <URL: http://www.youtube.com/watch?v=EjyyS1g07HM >.

Owlet; "What Do Those Lights Mean ?; " [Facebook]; (2021); 1 page; [Retrieved on Jan. 6, 2022]; retrieved from <URL: https://www/facebook.com/watch/?v=7679698800527505 >.

Reddit; "Help Me Find a Dream Sock Sensor for the Owlet Smart Sock;" Reddit r/HelpMeFind; (Jan. 10, 2022); 5 pages; [Retrieved on Jun. 1, 2022]; retrieved from <URL: https://www.reddit.com/r/HelpMeFind/comments/s0nt94/help_me_find_a_dream_sock_sensor_for_the_owlet/ >.

\* cited by examiner

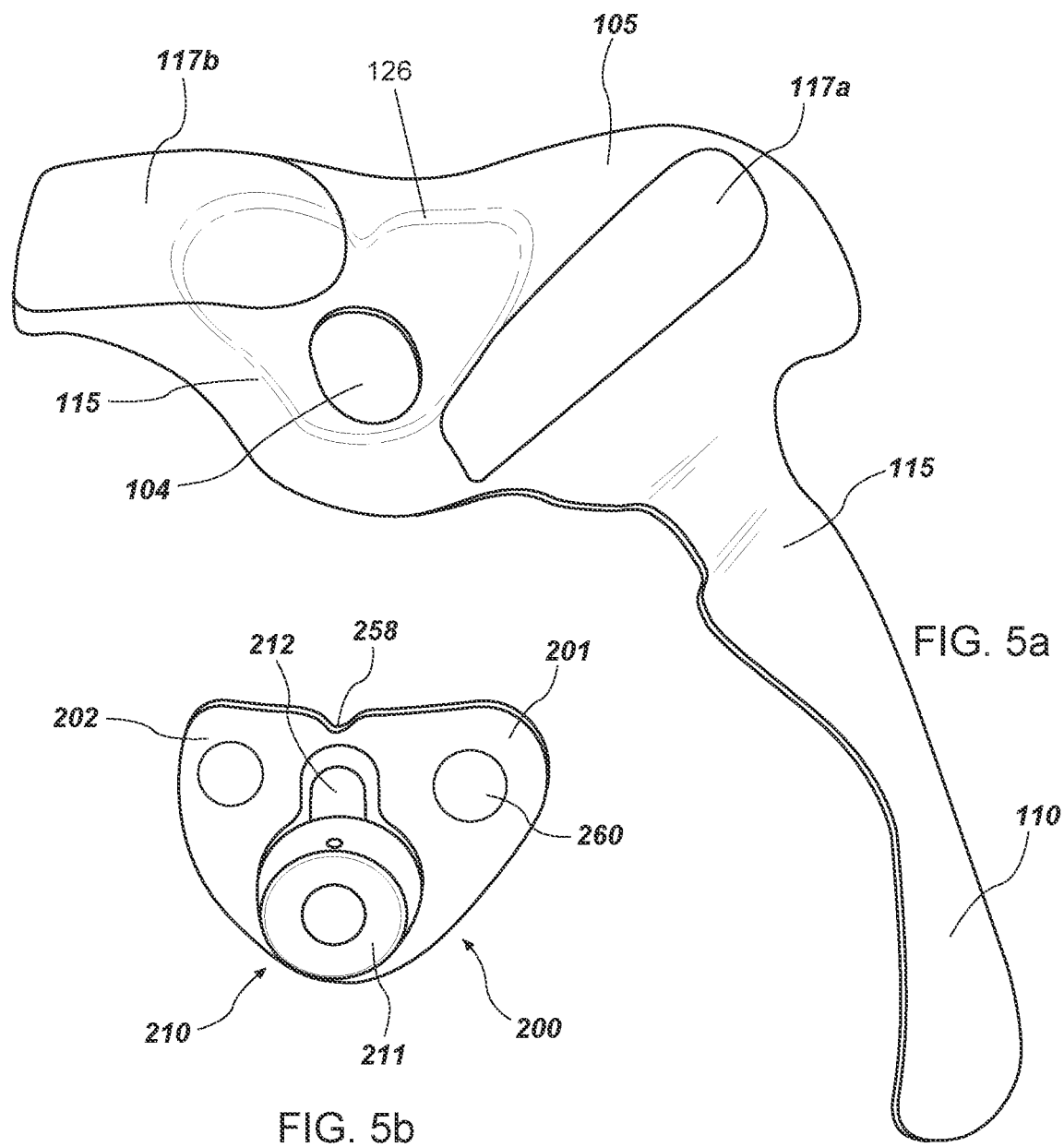

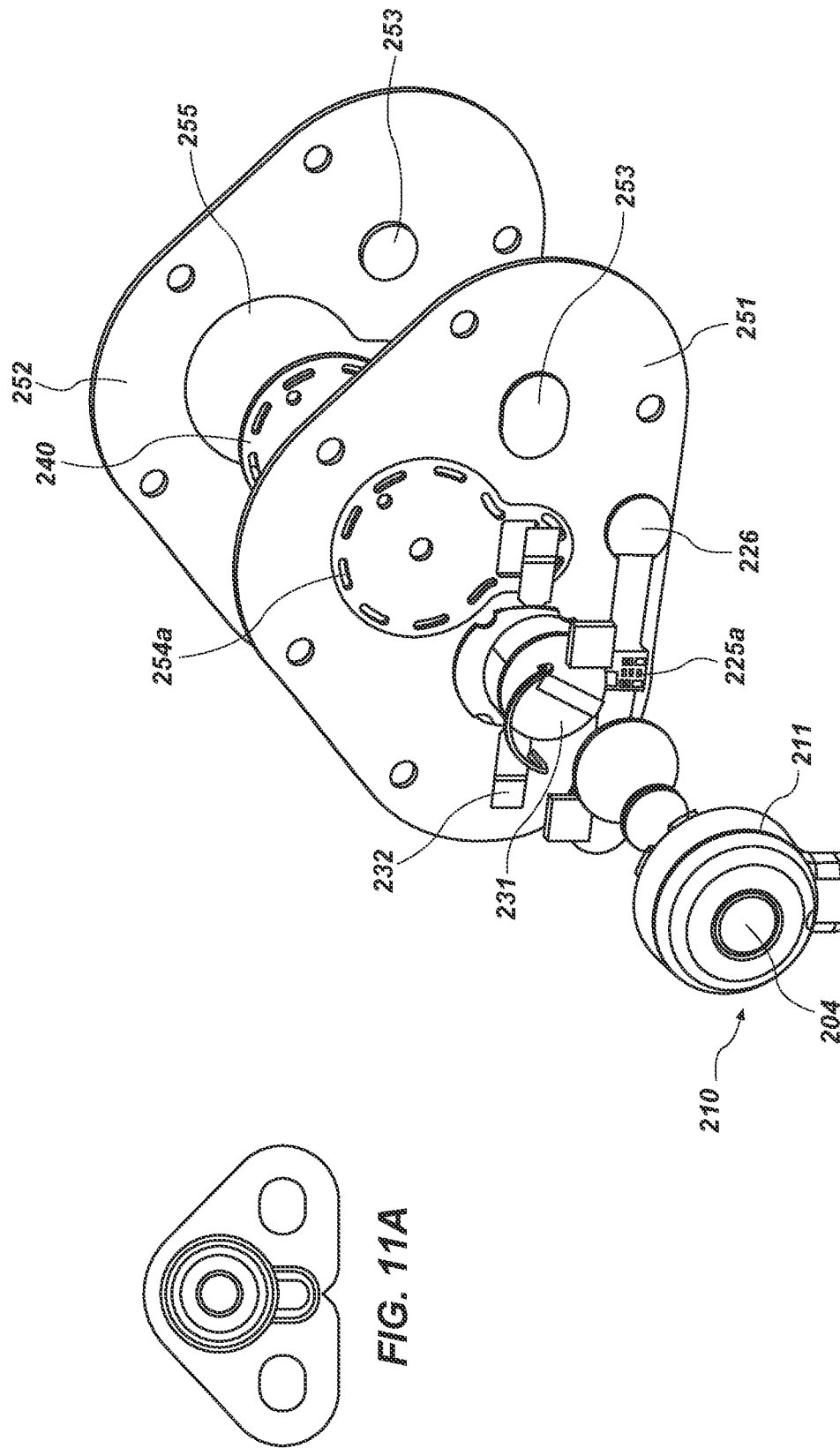

INFANT MONITORING DEVICE

PRIORITY CLAIM

This application claims priority to U.S. Ser. No. 63/042,203 entitled "Infant Monitoring Device" which was filed on Jun. 22, 2020 and is incorporated herein by reference in its entirety. This application also claims priority to U.S. Ser. No. 63/042,511 filed on Jun. 22, 2020 entitled "Monitoring Device" which is incorporated herein by reference in its entirety.

FIELD OF THE DISCLOSURE

Disclosure embodiments relate generally to monitoring devices, and more particularly to a wearable garment for monitoring infant data.

BACKGROUND

For many years, problems associated with Sudden Infant Death Syndrome (SIDS) have been addressed by the health community. SIDS is considered a significant cause of infant mortality during the first year of life. In many cases, SIDS is designated as the cause of death whenever a healthy infant dies suddenly during sleep for no apparent reason; though the cause of SIDS is allusive. Because infant survival can be improved if the onset of SIDS is detected, efforts have been expended in developing systems for monitoring an infant's heart rate, blood oxygen, or breathing rate during sleep. Systems for non-medical use have been developed, but have proven to be incapable of providing consistent, uniform, comfortable, and dependable monitoring of a child without suffering from false alarm signals. Therefore, it is one object of the present technology to provide a consistent, comfortable, and dependable health monitoring system which is employed for monitoring the overall health of an infant and, in some instances, producing an alarm signal whenever preset criteria are not met. Other and more specific objects will be described hereinafter.

SUMMARY

Aspects of the technology are directed towards a wireless monitoring sensor for monitoring biological data of an infant or other subject. Aspects of the technology include a sensing module that is removably disposed about a sock or garment or foot-band adapted to be placed about the foot of an infant, though in other applications the wearable monitor could be placed on other portions of the subject in other arrangements. The sensing module is configured to send wireless data to a base station and remote server and/or mobile device. The base station also acts as a recharging station for the sensing module 200 and notification station for providing a status indicator to a user.

BRIEF DESCRIPTION OF THE DRAWINGS

Technology embodiments will become more fully apparent from the following description, taken in conjunction with the accompanying drawings. It is to be understood that these drawings merely depict exemplary technology embodiments and are not to be considered limiting of the disclosure's scope. It will be readily appreciated that the components of the embodiments, as generally described and illustrated in the figures herein, could be arranged and designed in a wide variety of different configurations. Nonetheless, the technology will be described and explained with additional specificity and detail through the use of the accompanying drawings in which:

FIG. 5a is a perspective view of a portion of a monitoring device in accordance with one aspect of the technology;

FIG. 5b is a perspective view of a sensor module in accordance with one aspect of the technology;

FIG. 11a is a front view of a sensor module in accordance with one aspect of the technology;

FIG. 11b is an exploded view of a sensor module of a monitoring device in accordance with one aspect of the technology;

DESCRIPTION OF ASPECTS OF THE TECHNOLOGY

Figure 1:
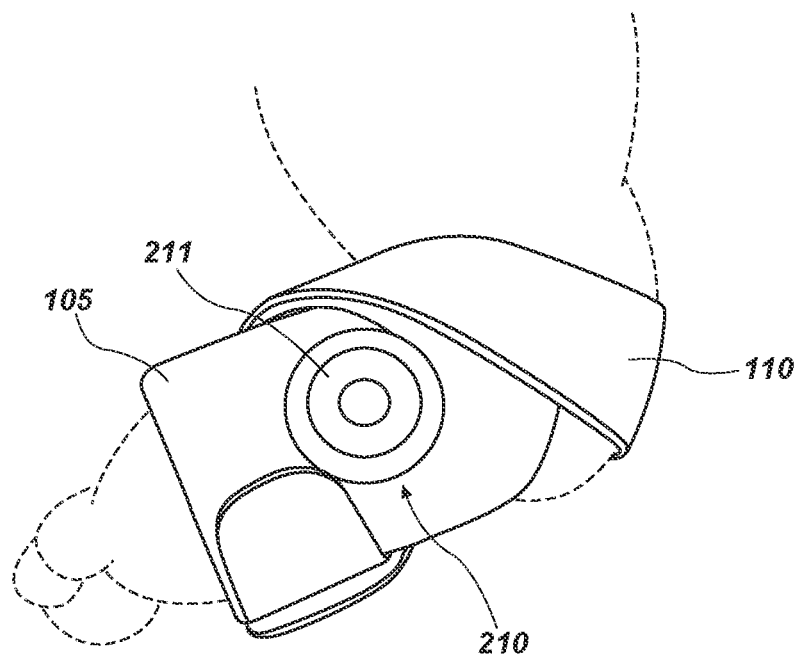
FIG. 1 is a perspective view of a monitoring device in accordance with one aspect of the technology.
Figure 2:
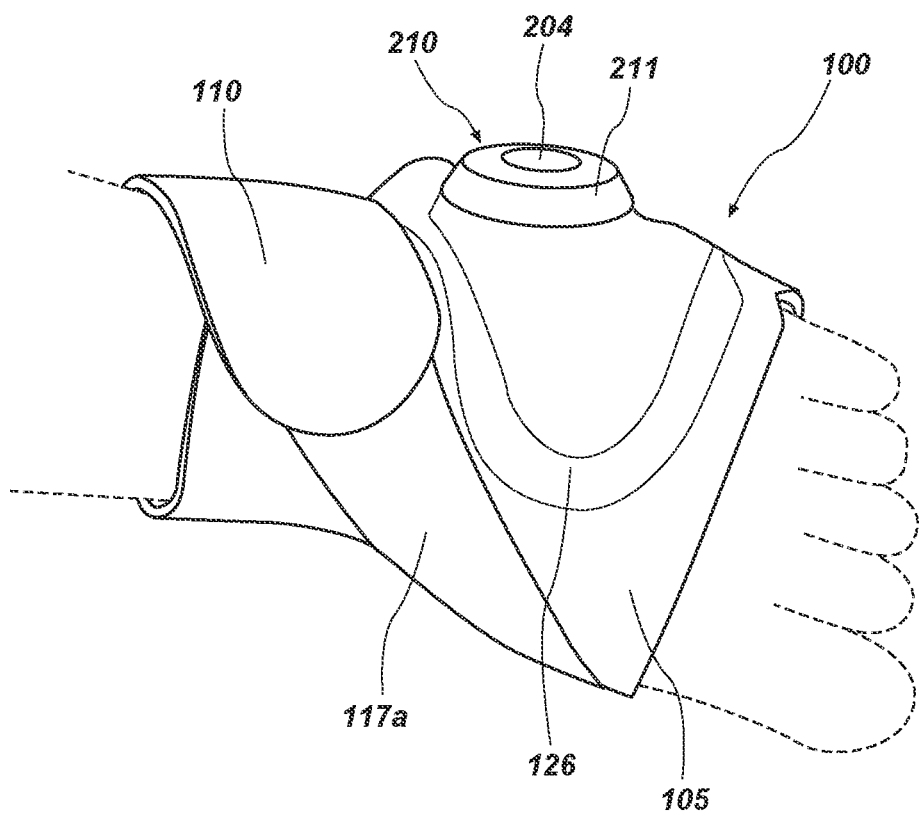
FIG. 2 is a perspective view of a monitoring device in accordance with one aspect of the technology.
Figure 3:
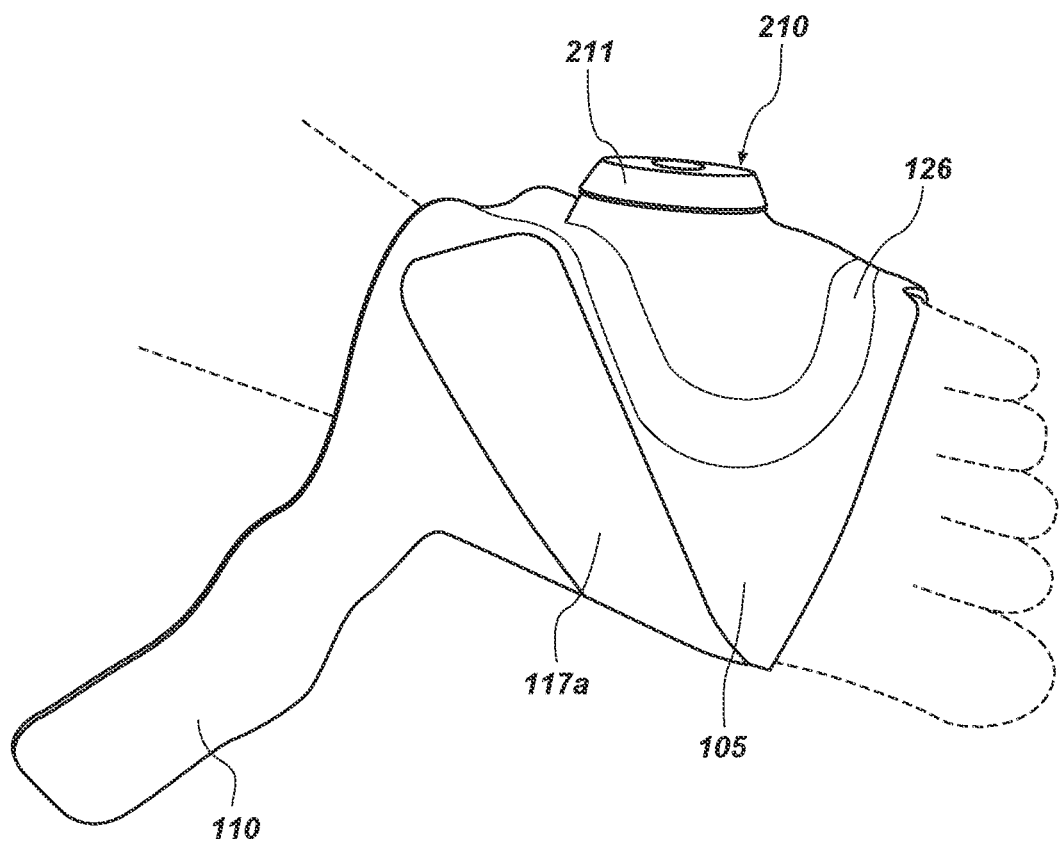
FIG. 3 is a perspective view of a monitoring device in accordance with one aspect of the technology.
Figure 4:
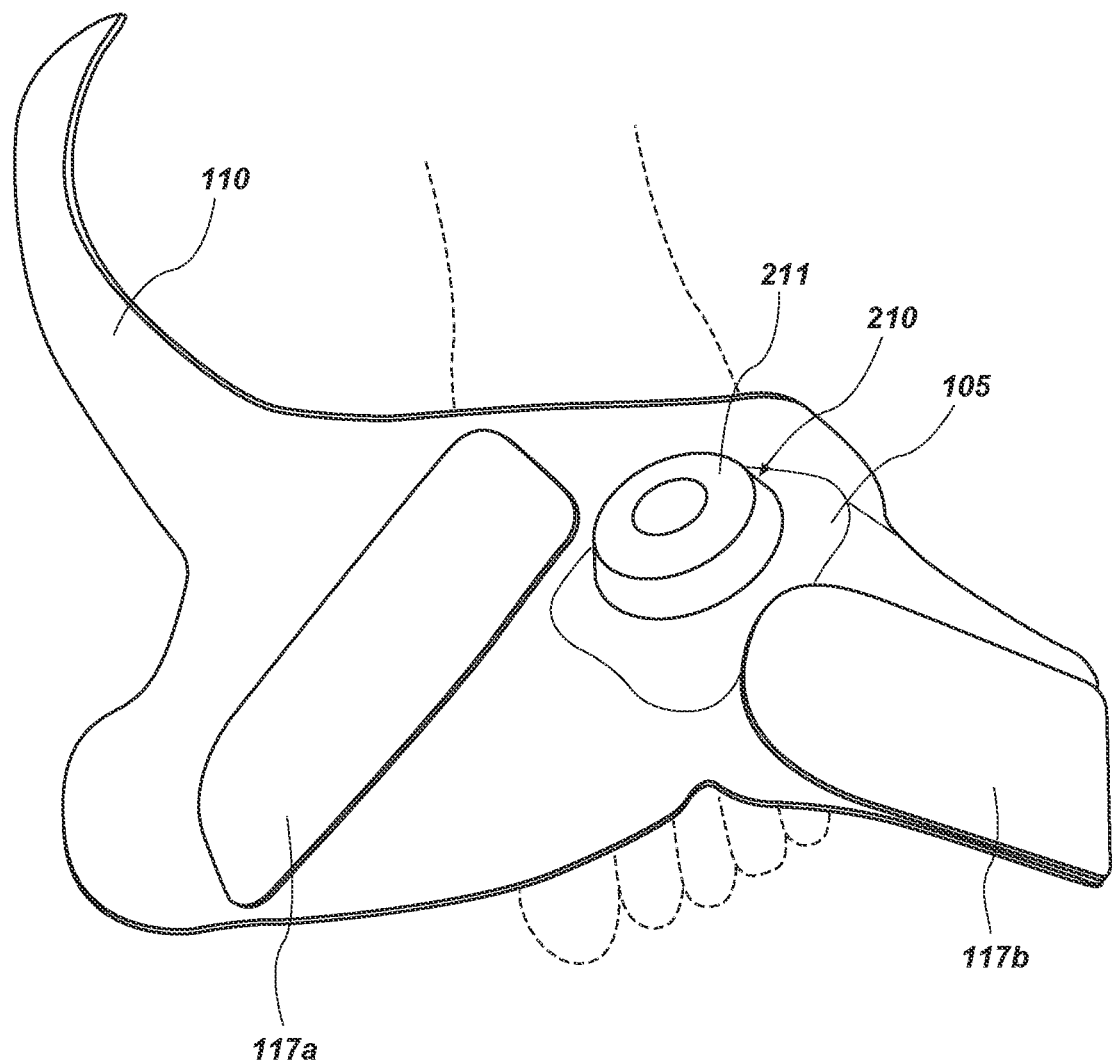
FIG. 4 is a perspective view of a monitoring device in accordance with one aspect of the technology.
Figure 6A:
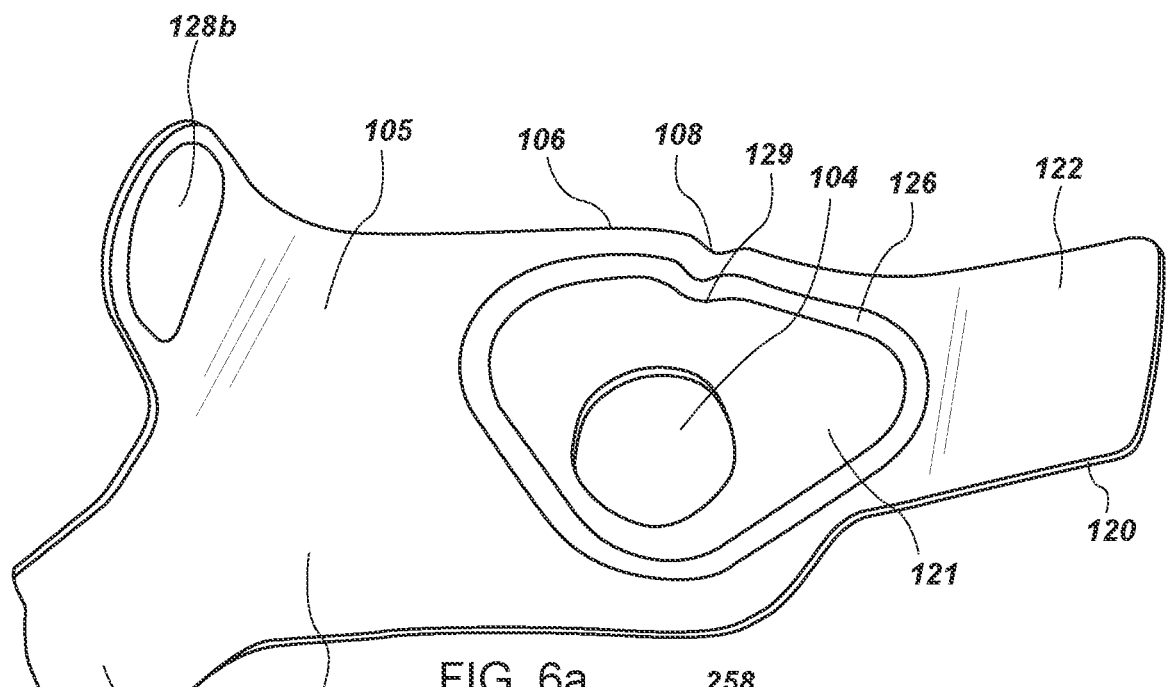
FIG. 6a is perspective view of a portion of a monitoring device in accordance with one aspect of the technology.
Figure 6B:
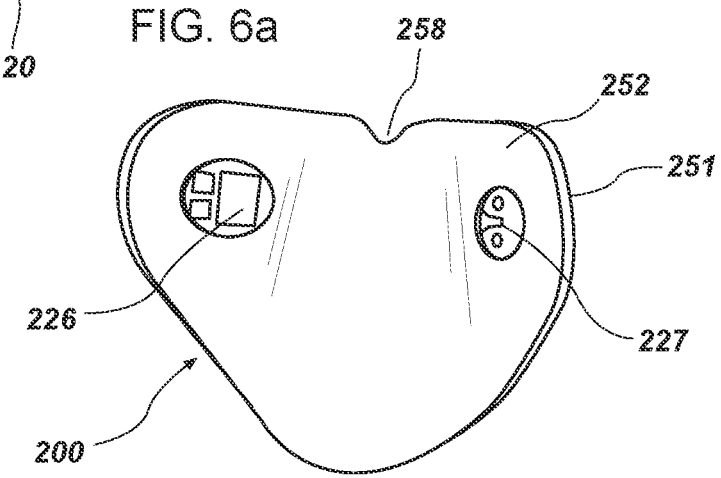
FIG. 6b is a perspective view of a back side of a sensor module in accordance with one aspect of the technology.
Figure 7:
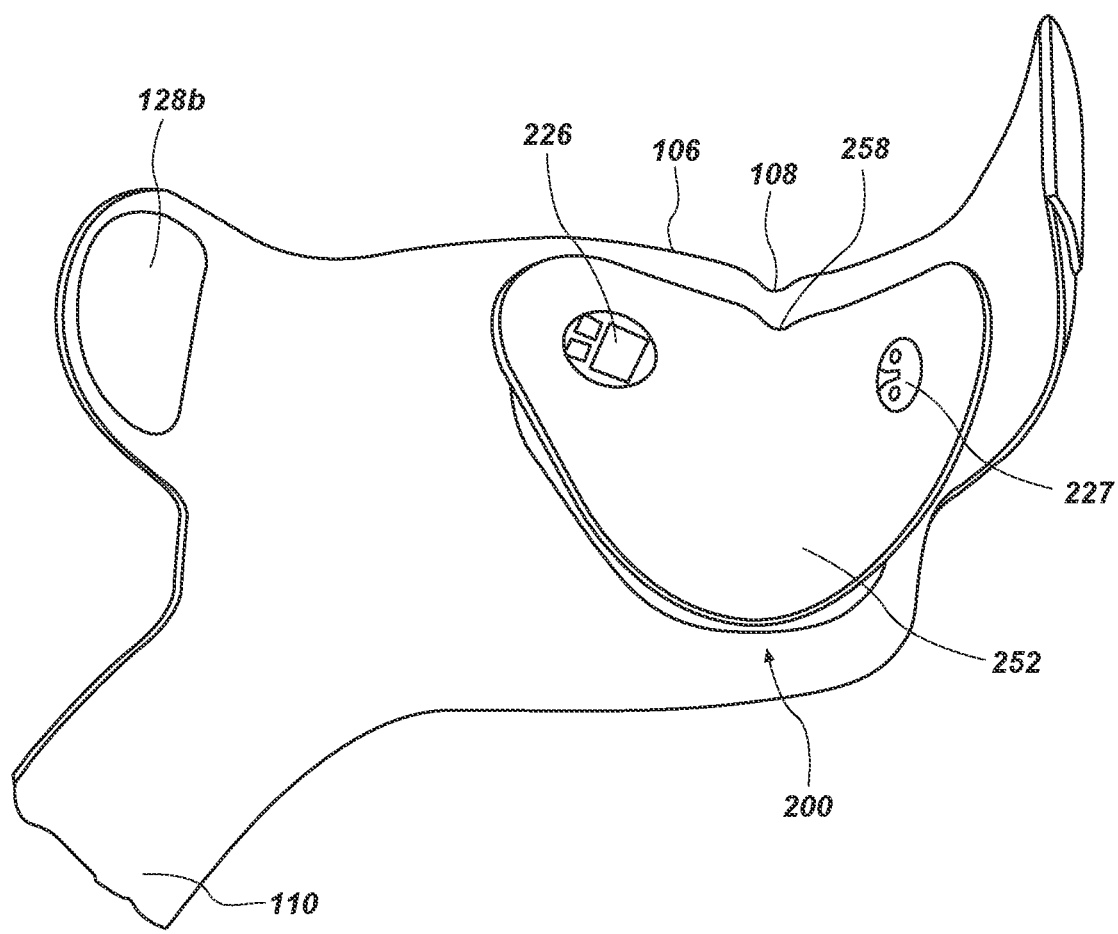
FIG. 7 is a perspective view of a monitoring device in accordance with one aspect of the technology.

The following detailed description includes reference to the accompanying drawings, which form a part hereof and in which are shown, by way of illustration, exemplary embodiments. However, before the present technology is disclosed and described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations. Unless defined otherwise, all technical and scientific terms used herein have the same meaning as commonly understood by one of ordinary skill in the art to which this disclosure belongs.

As used in this specification, the singular forms "a," "an" and "the" include plural referents unless the context clearly dictates otherwise. Thus, for example, reference to "a line" includes a plurality of such lines.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in this specification it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

The term "coupled," as used herein, is defined as directly or indirectly connected in a fluidic or non-fluidic manner.

Objects described herein as being "adjacent to" each other may be in physical contact with each other, in close proximity to each other, or in the same general region or area as each other, as appropriate for the context in which the phrase is used.

Occurrences of the phrase "in one embodiment," or "in one aspect," herein do not necessarily all refer to the same embodiment or aspect.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms."

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.8, 3, 3.1, 4, 4.6, and 5, individually.

This same principle applies to ranges reciting only one numerical value as a minimum or a maximum. Furthermore, such an interpretation should apply regardless of the breadth of the range or the characteristics being described.

As used herein, "enhanced," "improved," "performance-enhanced," "upgraded," "improvement," and the like, when used in connection with the description of a device, component, or process, refers to a characteristic of the device, component or process that provides measurably better form, function, or outcome as compared to previously known devices or processes. This applies both to the form and function of individual components in a device or process, as well as to such devices or processes as a whole.

Reference throughout this specification to "an example" means that a particular feature, structure, or characteristic described in connection with the example is included in at least one embodiment. Thus, appearances of the phrase "in an example" in various places throughout this specification are not necessarily all referring to the same embodiment.

The term "biocompatible material" refers to any material with the ability to act and perform without impairing basic immunological functions of the body. Typical biocompatible plastics, for example, include polyvinylchloride or PVC, polyether sulfone or PES, polytetrafluoroethylene or PTFE, polyethylene (PE-UHMW or PE-LD & HD), polyurethane or PU and the like.

Example Embodiments

It should be understood that the aspects of the technology discussed herein are contemplated for use with a wearable monitor. For purposes of illustrating the various aspects of the methods and systems claimed herein, the discussion below will be primarily directed to describing exemplary embodiments directed to a close-fitting garment worn by an infant or other person used to measure biological data of the wearer. It should be noted, however, that the elements and principles discussed herein are applicable to other applications. It is also noted that discussion of methods and systems herein can be interchangeable with respect to specific aspects. In other words, specific discussion of one apparatus, method, or system (or components thereof) herein is equally applicable to other aspects as they relate to the system, apparatus, or methods, and vice versa.

An initial overview of technology embodiments is provided below and specific technology embodiments are then described in further detail. This initial summary is intended to aid readers in understanding the technology more quickly, but is not intended to identify key or essential technological features, nor is it intended to limit the scope of the subject matter. In particular, aspects of the technology are directed towards a wireless monitoring sensor for monitoring biological data of an infant or other subject. Aspects of the technology include a sensing module 200 that is removably disposed about a sock or garment 100 or foot-band adapted to be placed about the foot of an infant, though in other applications the wearable monitor could be placed on other portions of the subject in other arrangements. The sensing module 200 is configured to send wireless data to a base station 300 and remote server and/or mobile device. The base station 300 also acts as a recharging station for the sensing module 200 and notification station for providing a status indicator to a user.

Sock or Garment Configuration

In one aspect of the technology, the fabric of the sock 100 may be a stretchable fabric, for example a woven elastomer in the class of segmented co-polyesters such as polyester-polyurethane copolymer fibers alone or blended with cotton or other natural fibers or synthetic polymer fibers such as polyester, nylon, acrylic, and the like. For example, in one aspect of the technology, the fabric of the garment comprises a nylon, polyester, spandex blend. The fabric is configured to wrap around the foot (or other body part) of an infant (or other subject) and couple to itself using hook and loop fasteners, snaps, zippers, belts, velcro, or other fasteners known in the art.

Figure 8:
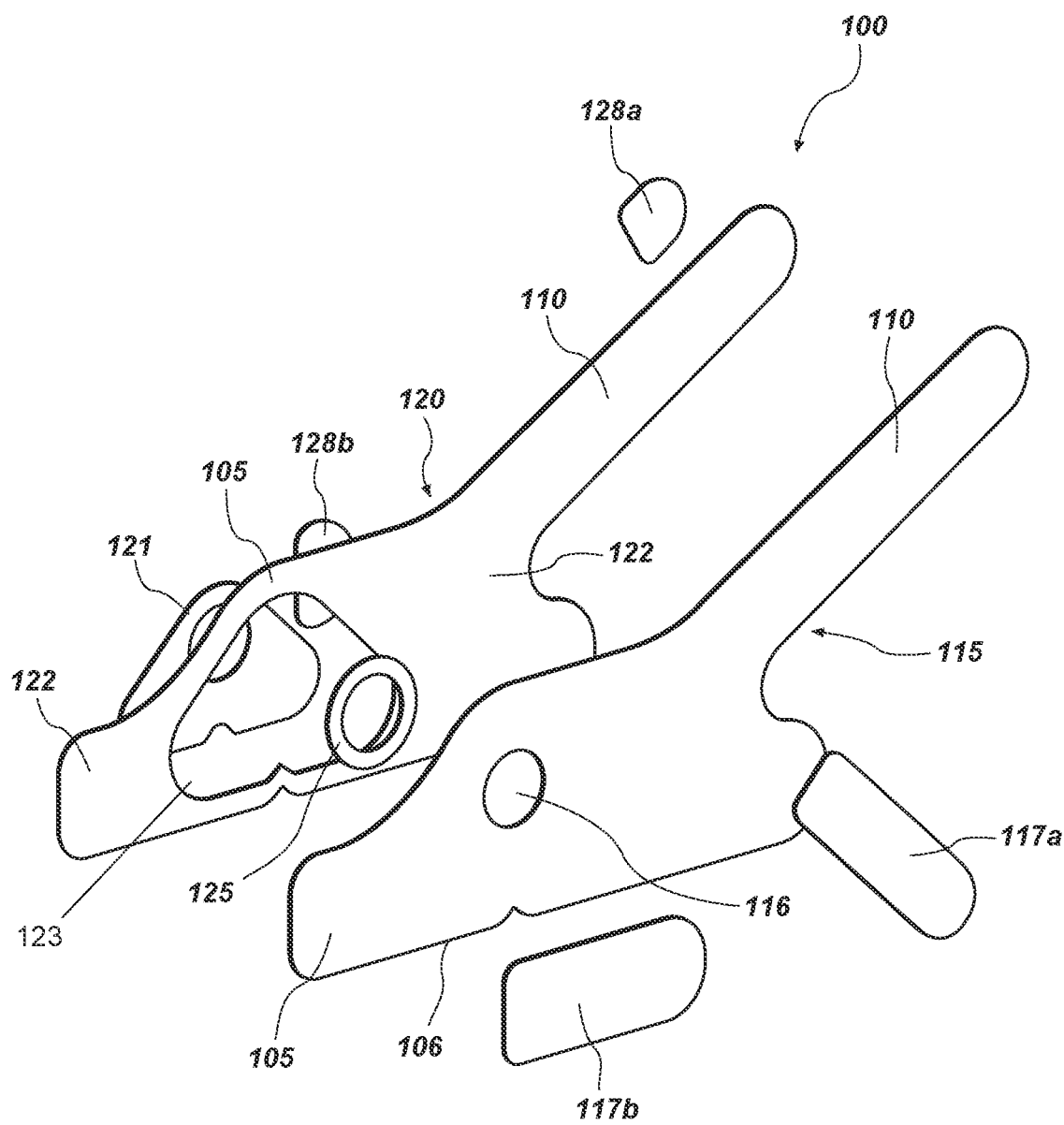
FIG. 8 is an exploded view of a garment portion of a monitoring device in accordance with one aspect of the technology.
Figure 9:
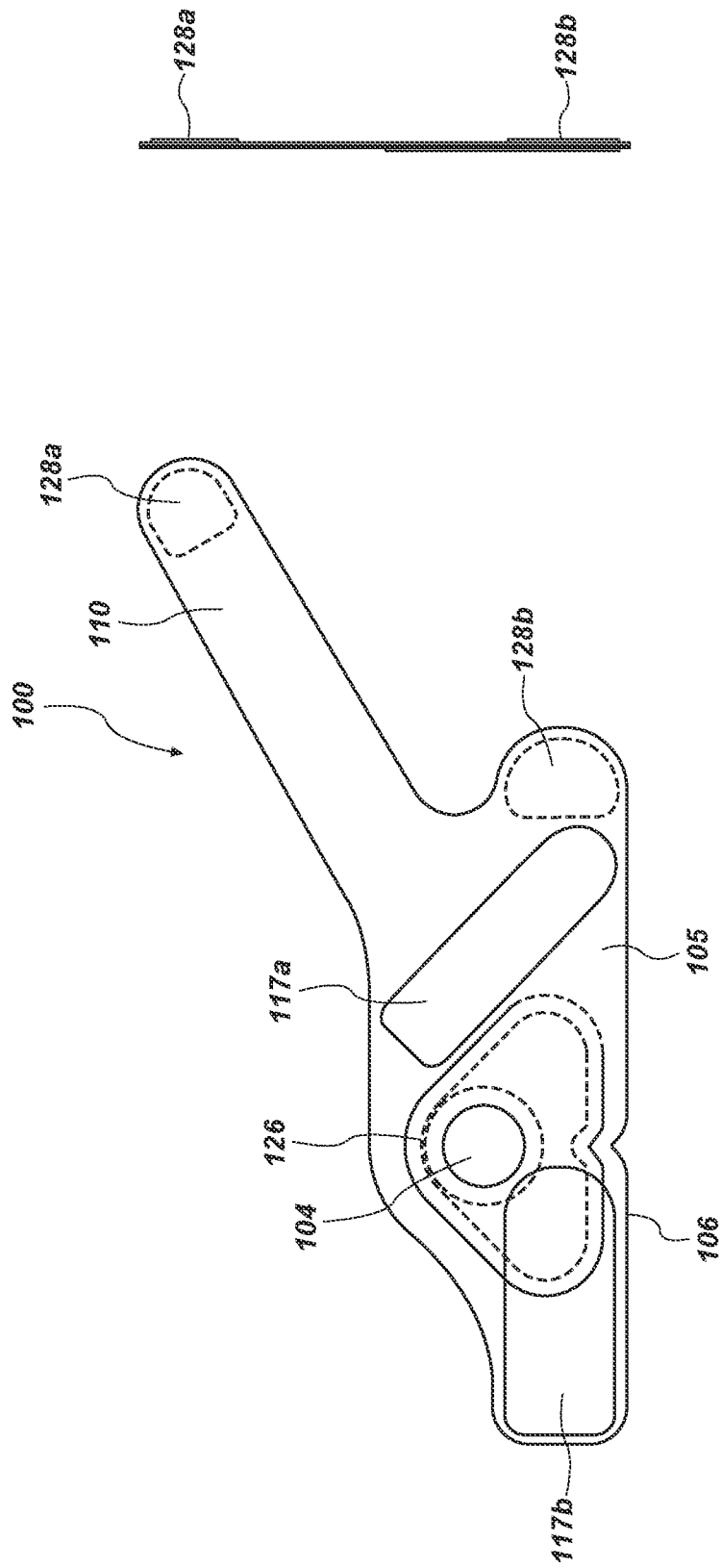
FIG. 9a is a side view of a garment portion of a monitoring device in accordance with one aspect of the technology.
FIG. 9b is a side view of a garment portion of a monitoring device in accordance with one aspect of the technology.
Figure 10:
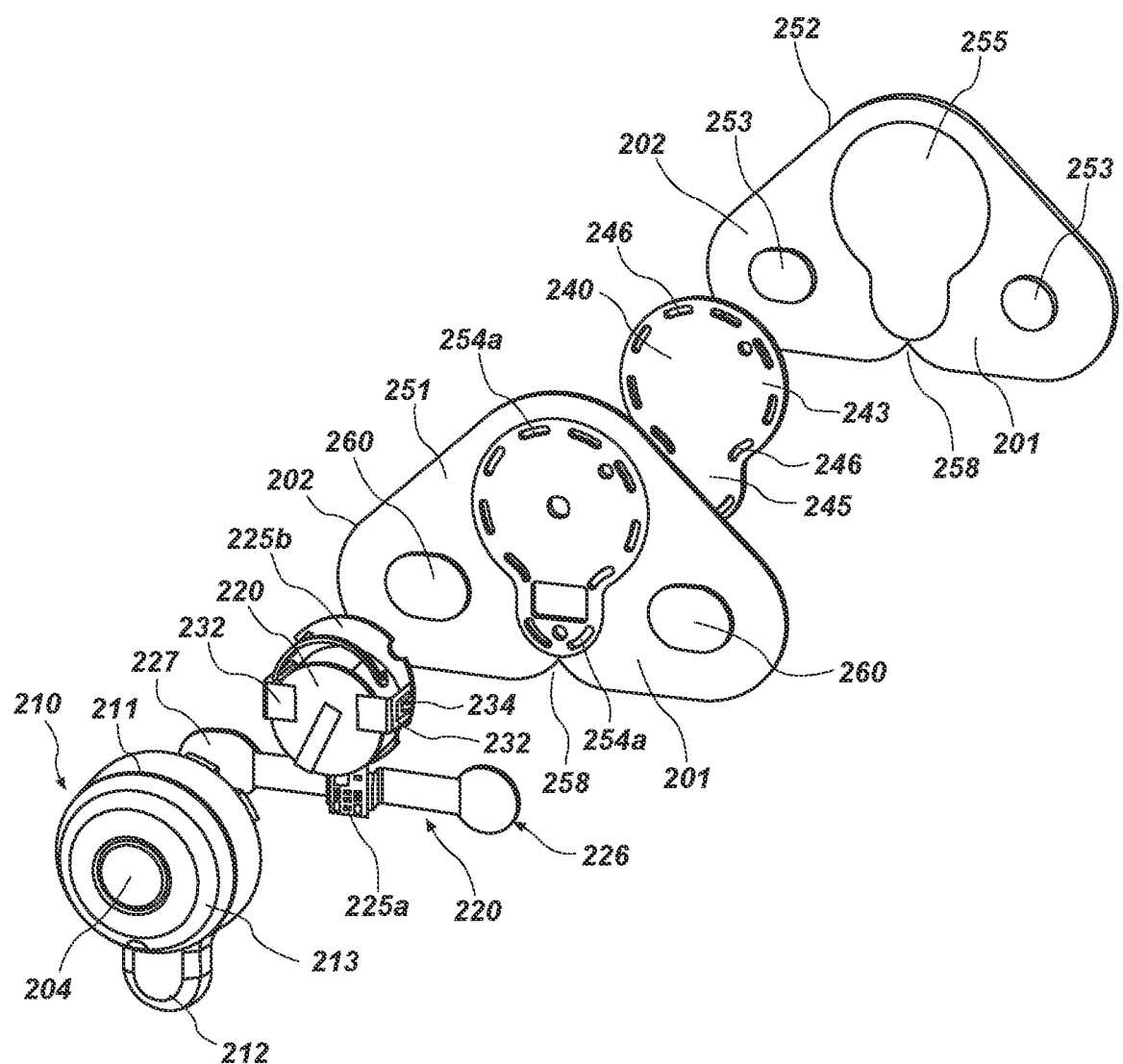
FIG. 10 is an exploded view of an assembly of a sensor module of a monitoring device in accordance with one aspect of the technology.
Figure 12C:
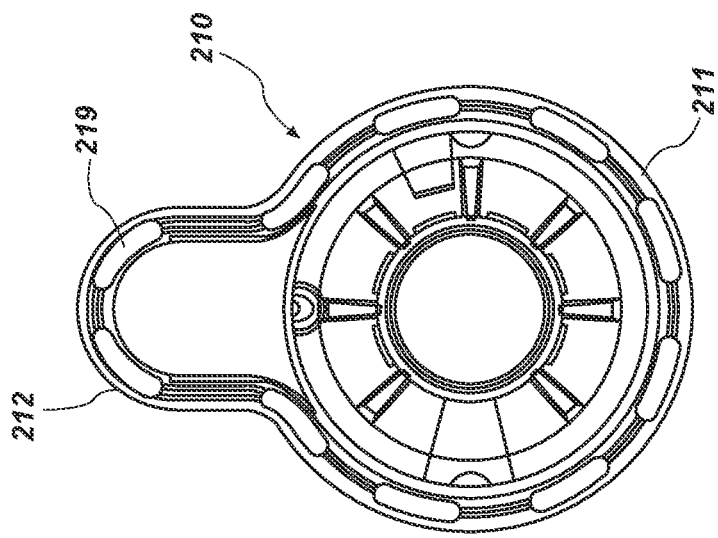
FIG. 12c is a back view of a portion of an enclosure of a monitoring device in accordance with one aspect of the technology.
Figure 12B:
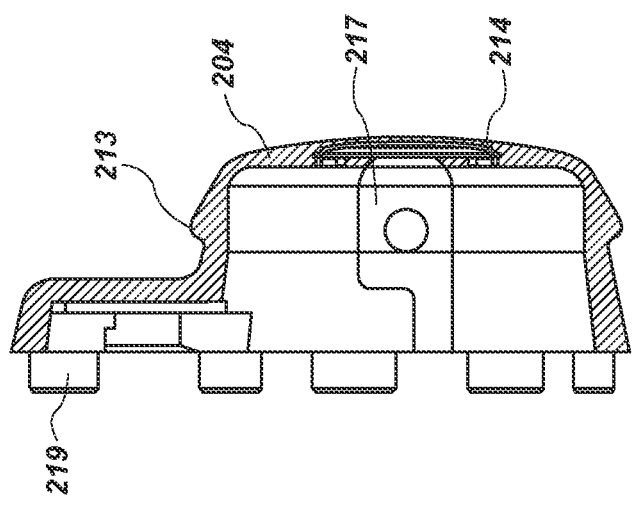
FIG. 12b is a side view of a portion of an enclosure of a monitoring device in accordance with one aspect of the technology.
Figure 12A:
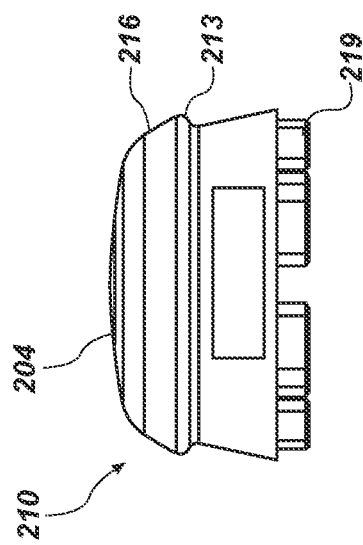
FIG. 12a is a side view of a portion of an enclosure of a monitoring device in accordance with one aspect of the technology.
Figure 13B:
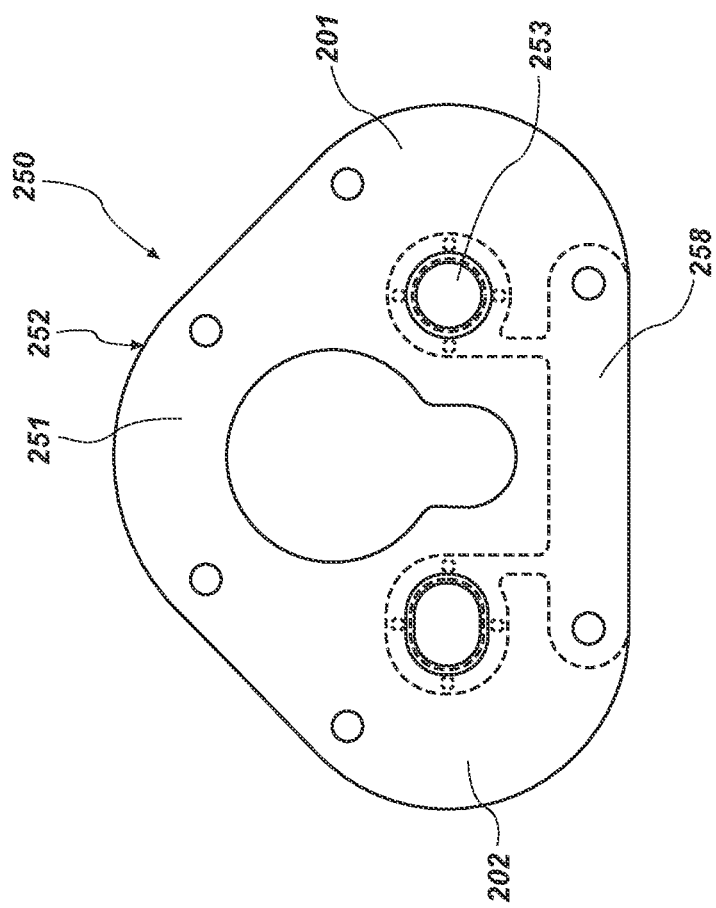
FIG. 13b is a back view of a fabric enclosure of a monitoring device in accordance with one aspect of the technology.
Figure 13A:
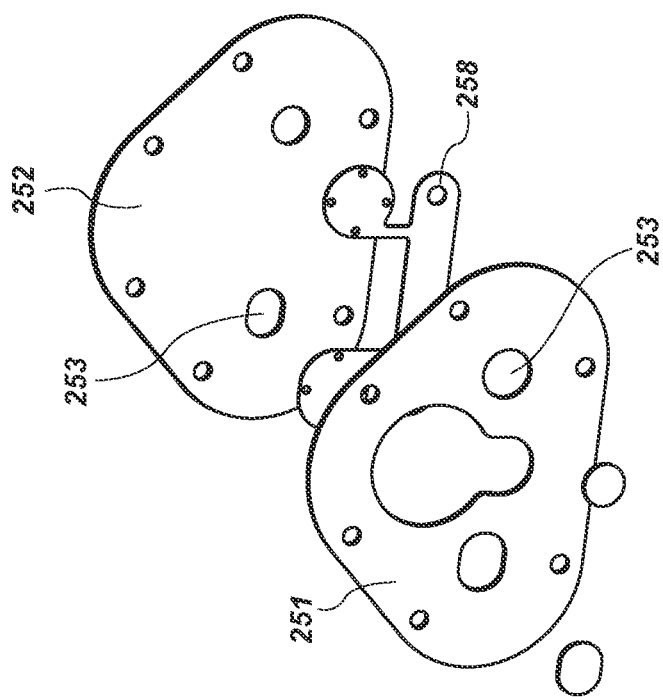
FIG. 13a is an exploded view of a fabric enclosure of a monitoring device in accordance with one aspect of the technology.
Figure 14C:
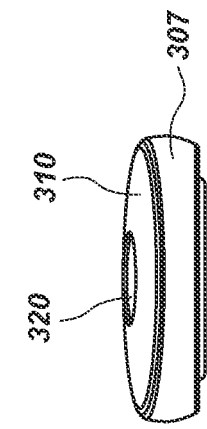
FIG. 14c is a side view of a base station in accordance with one aspect of the technology.
Figure 14B:
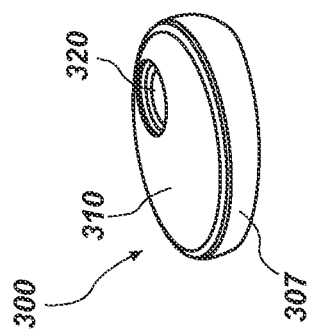
FIG. 14b is a perspective view of a base station in accordance with one aspect of the technology.
Figure 14D:
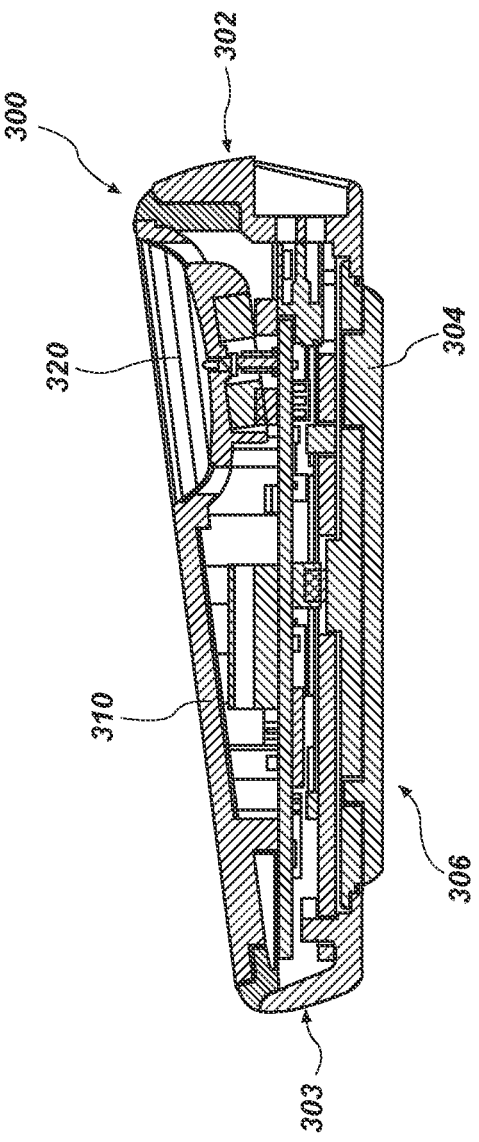
FIG. 14d is a cross sectional side view of a base station in accordance with one aspect of the technology.
Figure 14A:
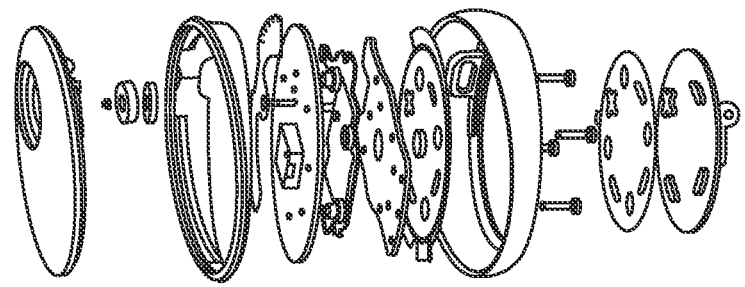
FIG. 14a is an exploded view of a base station in accordance with one aspect of the technology.

With reference to FIGS. 8 and 9 (and generally to FIGS. 1-7), the sock 100 or garment comprises a generally planar material having a first portion 105 or base member/base portion configured to wrap around the foot (or other body part) of an infant (or other subject) and a second portion or strap 110 extending above and away from the first portion 105, the second portion 110 being configured to wrap around the leg and/or ankle of the infant (or other body part of a subject, e.g., an arm or hand). In one aspect of the technology, the first portion 105 comprises a longitudinal axis that is substantially parallel to a bottom edge 106 of the first portion 105. The second portion 110 or strap extends upward from a top portion 111 of the second portion at an axis that is greater than about 45 degrees relative to an axis normal to the longitudinal axis of the first portion 105 (i.e., normal to the bottom edge 106). In another aspect, however, the second portion extends from the top portion 111 at an angle that ranges from between 20 and 60 degrees, 45 and 55 degrees, 45 and 65 degrees, or 45 and 75 degrees relative to the axis normal to the longitudinal axis of the first portion 105.

In one aspect of the technology, the first portion 105 and the second portion 110 comprise a plurality of elastic, stretchable, or flexible fabric components. In one aspect, the sock or garment 100 comprises an outward layer 115 and an inner layer 120 both making up the first portion 105 and second portion 110. The outward layer 115 comprises a first stretchable material having a through-hole 116 disposed about the first portion 105. In one aspect, the outward layer 115 also comprises fasteners 117a, 117b disposed about a lateral side 118 of the outward layer 115 and about a lateral side of the through-hole 116 and is continuous in that it comprises a single piece of fabric or multiple pieces of fabric without any substantial gap therebetween. In other aspect, the inner layer 120 is discontinuous in that it comprises two pieces of a flexible fabric, an inner portion 121 and outer portion 122. The inner portion 121 is generally triangular shaped, though it can be any shape (i.e., rectangular, oval, etc.) suitable to accommodate placement of the sensor module 200 or as suits a particular purpose. The outer portion 122 approximates the general shape of the outer layer 115 but for a void 123 that approximates the shape of the inner portion 121. The void 123 of the inner portion 121 of the inner layer 120 is larger (i.e., has a greater area) than the inner portion 121 leaving a flexing area 126 between inner portion 121 and the outer portion 122. In one aspect, the fabric of the inner layer 120 is less stretchable or elastic than the fabric of the outer layer 115. In this manner, when the outer layer 115 and the inner layer 120 are adhered together, the inner portion 121 is able to flex thus accommodating placement of the sensor module 200 about the foot of the infant or other body part of a subject. In one aspect of the technology, the inner portion 121 comprises a through-hole 124 that approximates the size and shape of the through-hole 116. A ring 125 is disposed between the outer layer 115 and the inner portion 121 to stabilize the through-hole 124 created in the sock or garment 100. The diameter of the ring 125 is substantially similar to the diameter of the through-hole 116 and through-hole 124. In one aspect of the technology, the inner layer comprises fasteners 128a, 128b that are intended to couple with fasteners 117a, 117b as the sock or garment 100 is placed about the foot of the infant. Fastener 128a couples with fastener 117a and fastener 128b couples with fastener 117b. While hook and loop (i.e., velcro) fasteners are disclosed, it is understood that many different types of fasteners can comprise many different types of fasteners known in the art without departing from the scope of the technology.

In one aspect of the technology, the sock or garment 100 is placed on the foot of the infant with bottom edge 106 towards the toe of the infant. A notch 108 is located on the bottom edge 106 of the sock 100 corresponding to a notch 129 in the inner portion 121 of the inner layer 120. In one aspect of the technology, the different notches are lined up with the bottom edge of the foot of the infant as the sock 100 is placed on the infant to ensure proper placement of the sensor module 200 on the foot. A corresponding notch 258 is located in the fabric enclosure 250 of the sensor module 200 to ensure the sensor module 200 is properly aligned with the sock 100.

Sensor Module

With reference generally to FIGS. 10 through 13, in one aspect of the technology, a sensor module or sensing module 200 is configured to couple to the sock or garment 100 such that when the sock 100 is properly placed on the foot of the infant, data with respect to the infant (e.g., temperature, heart-rate, blood oxygen, etc.) may be obtained. The general shape of the sensor module 200, when positioned on the sock 100, advantageously positions the sensors about an exterior portion of the infant's foot for optimal measurement of important biological data. For example, sensor module or sensing module 200 comprises opposing wings 201, 202 that house sensors configured to propagate light onto the skin of the infant as well as through the skin of the infant. Sensors on one wing 201 propagate light, while sensors on the other wing 202 measure light that is transmitted through the foot of the infant. In one aspect, the sensor module 200 is generally triangular shaped, but it is understood that it may comprise other shapes (e.g., rectangular, oval, etc.) as suits a particular application. In one aspect of the technology, the triangular shape of the sensor module 200 efficiently houses the electronics sub-assembly 220 and provides for optimal placement of the sensors about the foot (or other tissue) of the subject.

In one aspect of the technology, the sensor module 200 comprises a contact charging enclosure 210, an electronics sub-assembly 220, an attachment plate 240, and a fabric enclosure 250. In one aspect, the fabric enclosure comprises a top piece 251 (or top layer of the fabric enclosure 250) and bottom piece 252 (or bottom layer of fabric enclosure 250) that are generally triangular. In one aspect, the bottom piece 252 comprises soil release and antimicrobial coatings. Each of the top and bottom pieces 251, 252 are sized to approximate the void 123 of the inner layer. The top piece 251 and bottom piece each comprise through-holes 253 on lateral sides of the enclosure 250. The through-holes 253 create a pathway for the transmission of light (or other thermal or electromagnetic waves) from the sensor electronics. In one aspect, a front side of the through-holes are covered with a transparent window to permit light transmission, while a back side of the through-holes 253 (i.e., the back side of the sensors) include a fastener 260 for coupling the fabric enclosure 250 to the inner portion 121 of inner layer 120. Advantageously, with the fasteners disposed about the fabric enclosure 250 behind the sensors, the location of the sensors with respect to the foot of the infant as the sock is placed on the foot of the infant (or other body part of a wearer) is optimized.

In one aspect of the technology, the top piece 251 also includes a plurality of apertures 254 that correspond to plastic pins 219 from the enclosure 210. The pins 219 of the enclosure 210 pass through the apertures 254 of the top piece and into corresponding apertures 246 of the attachment plate 240. An aperture 254a is also located in the top piece 251 to accommodate a portion of the electronics sub-assembly 220. The bottom piece 252 of the fabric enclosure includes a void 255 that is shaped to approximate the attachment plate 240. However the void 255 does not extend through the entire bottom piece 252 like the apertures 254 extend through the top piece 251. Rather, the void 255 comprises a thinned area of the bottom piece 252 in which the attachment plate 240 is placed.

In one aspect of the technology, the through-holes 253 comprise a transparent thermoplastic insert 258 (e.g., Technomelt PA-668, etc.) or other transparent window. The top piece 251 secures the window film, the attachment plate 240, the electronics sub assembly 220, and the charging enclosure 210. Hotmelt adhesive is used to couple the top piece 251 to the bottom piece 252 and also adds water resistance around the sensors to prevent moisture damage during use. In other words, the fabric layers are bonded together using a secure adhesive activated with heat. Disposing the fabrics in this arrangement allows the sensor module 200 to remain safe while being flexible and soft.

In one aspect of the technology, the attachment plate 240 comprises stainless steel plate (or other conductive material, such as copper, conductive plastics, or combinations of materials) with a plurality of apertures 246 about the perimeter of the plate 240. The attachment plate 240 is "mushroom" shaped in that it comprises a generally larger top portion 243 coupled to a smaller bottom portion 244 extending downward from the top portion 243. In one aspect, the top portion 243 is generally circular and the bottom portion 244 is likewise curvilinear. The shape of the attachment plate 240 approximates the general shape of the contact charging enclosure 210.

Generally speaking, the sensor module 200 is configured to "snap fit," push fit, or friction fit into through-hole 104 of the sock or garment 100 from the bottom up by way of the top portion of the charging enclosure 210. The garment 100 is flexible enough to allow a portion of the sensor module 200 to push more easily through the through-hole 104 in a first direction than being pulled back through the through-hole 104 in the opposite direction. The enclosure 210 is also generally "mushroom" shaped in that it comprises a larger top portion 211 and smaller bottom portion 212 extending downward from the top portion 211. The top portion 211 is disposed near the top of the triangular-shaped sensor module 200 and the bottom portion 212 is disposed near the base of the sensor module 200 allowing for the sensors (or sensor assemblies) 226, 227 to be located about the wings 201, 202 of the sensor module 200. The top portion 211 has an internal volume that is larger than an internal volume of the bottom portion 212 to accommodate different portions of the electronics sub-assembly 220.

In one aspect of the technology, the top portion 211 comprises a ridge 213 that circumscribes an outer perimeter of the top portion 211 and is configured to removably fit through the though-hole 104 and help to retain the sensor module 200 within the sock or garment 100. While a ridge 213 is disclosed, it is understood that other mechanisms for temporarily attaching the sensor module 200 to the sock 100 are contemplated, including, but without limitation, rigid tabs and corresponding channels, threaded fasteners, or the like. Moreover, the ridge 213 need not continuously circumscribe the outer perimeter of the top portion 211, but may comprise intermittent ridges with that partially circumscribe the outer perimeter of the top portion sufficient to temporarily retain the top portion 211 through the through-hole 104. The circumference or outer perimeter of the ridge 213 is greater than the inner perimeter of the through-hole 104, while the areas of the enclosure on either side of the ridge 213 have a perimeter that is similar to the inner perimeter of the through-hole 104 or, on the distal side of the ridge 213 (i.e., the side nearest the nose 204), the ridge 213 tapers 216 to a smaller outer perimeter to facilitate placement of the top portion 211 of the enclosure 210 through the through-hole 104. Advantageously, the ridge 213 assists in maintaining the general location of the sensor module 220 on the sock 100 while the additional fasteners located behind the sensors on the fabric enclosure 250 assist in keeping the sensor module 200 from rotating within the through-hole 104 while the sock 100 is being placed or is worn. The coupling of the sensor module 200 in this manner to the sock, in connection with the flexing area 126 of the sock 100, optimizes comfort and proper positioning of the sensor module 220 on the foot of the infant.

In one aspect of the technology, the enclosure 210 comprises a plastic material with insert molded contact pins 217 and a rigid nose 204 that is electrically coupled to the electronics sub-assembly 220. In one aspect, the nose 204 comprises a molded charging contact 214. It also includes a bent-wire RF antenna that is coupled to the electronics sub-assembly 220 configured to transmit data received from the sensors to a remote processor, remote server, cloud-based system, or other remote storage/processing device. A magnet is disposed within the top portion 211 for coupling with the base station 300 to facilitate proper charging of the battery 231. An antenna (e.g., an inverted F-wire antenna, etc.) is disposed about the battery 231. The bottom portion 212 of the enclosure 210 has an internal volume that is less than the internal volume of the top portion 211. The bottom portion 212 is configured to house portions of a PCB 225a that couple with sensors 226, 227 disposed within the wings 201 and 202. The PCB 225a couples to the sensors (or sensor assemblies) 226, 227 by way of a flexible polyester film 229 that houses conductive lines coupling the sensors 226, 227 to the PCB 225a. When the fabric enclosure 250 is disposed about the electronics sub-assembly 220, the sensors (or sensor assemblies) 226, 227 are oriented so that the light propagated from the sensors is directed through the apertures 253, and the light receiving components of the sensors receive light through a corresponding aperture.

In one aspect, the electronics sub-assembly 220 comprises a battery 231 and two flexible PCB traces 232 skirt up the side of the battery 231 and secured to the top with tape. The PCB traces 232 couple to PCB 225b located on a back side of the electronics sub assembly 220. This portion of the electronics sub-assembly 220 is housed within the top portion 211 of the enclosure 210. The flexible traces 232 have a spring contact pin 234 that presses against the internal wall of the enclosure 210. The enclosure 210 comprises insert molded pins 217 with an exposed face on the inside and outside of the enclosure 210. The spring pins 234 contact the insert molded pins and allow electrical contact from the PCB on the inside surface of the enclosure 210 to the outside. One of the two pins is exposed centered at the apex of the enclosure dome 216. The other pin is exposed offset of that center pin. This offset pin is slightly protruding out the side of the enclosure 210. In another aspect of the technology, the enclosure 210 is molded with a nose 204. This nose 204 is rigid and helps to protect the analog front end of the electronics sub-assembly 220 which is susceptible to failure if the board is flexed.

The printed circuit board or PCB of the electronics sub-assembly 220 contains memory and programming instructions for storing information used for delivering a signal to the sensors and recording data received from the sensors. Memory refers to electronic circuitry that allows information, typically computer data, to be stored and retrieved. Memory can refer to external devices or systems, for example, disk drives or other digital media. Memory can also refer to fast semiconductor storage, for example, Random Access Memory (RAM) or various forms of Read Only Memory (ROM) that are directly connected to the processor. Computer terminals represent any type of device that can access a computer network. Devices such as PDA's (personal digital assistants), cell phones, personal computers, lap top computers, tablet computers, mobile devices, or the like could be used to access information produced by the sensor module. The computer terminals will typically have a display device and one or more input devices. The network may include any type of electronically connected group of computers including, for instance, Internet, Intranet, Local Area Networks (LAN), or Wide Area Networks (WAN). In addition, the connectivity to the network may be, for example, remote modem or Ethernet.

Base Station

Figure 15B:
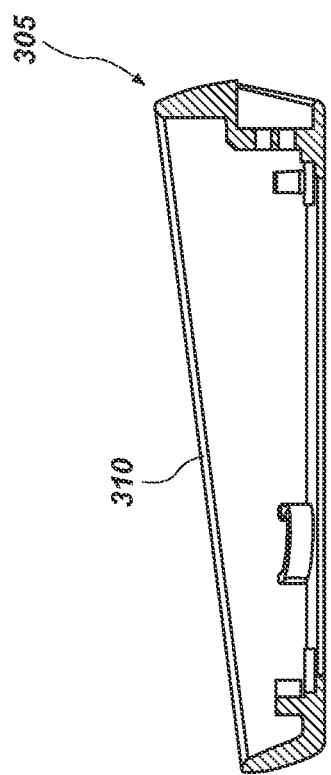
FIG. 15b is a cross-sectional side view of a portion of a base station in accordance with one aspect of the technology.
Figure 15A:
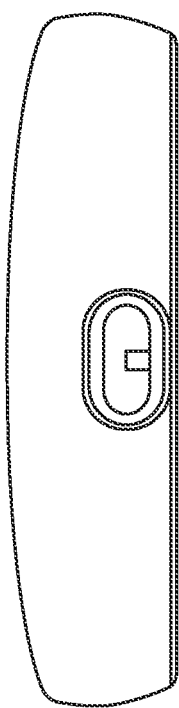
FIG. 15a is a backside view of a base station in accordance with one aspect of the technology.
Figure 16:
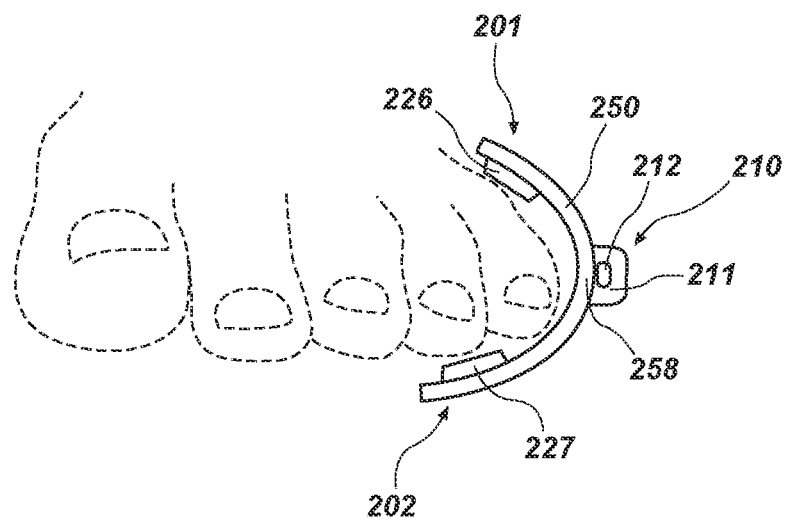
FIG. 16 is a view of a monitoring device in accordance with one aspect of the technology.

With reference generally to FIGS. 14 through 15, in aspects of the technology, the sensor module 200 is configured to couple a base station 300. The sensor module 220 couples to the base station wirelessly as well as physically to perform various functions. In one aspect of the technology, the sensor module 200 communicates directly with the base station 300 to relay information with respect to the infant (or other subject). In another aspect, the sensor module 200 communicates with a remote server or remote storage system or process which then communicates with the base station 300. The base station 300 comprises a wireless transmitter and wireless receiver configured to communicate with the remote device and/or sensor module 200. In another aspect, the sensor module 200 may physically couple with the base station 300. In any event, the sensor module 200 relays information to the base station 300 and receives information from the base station 300, either directly or indirectly.

In one aspect of the technology, the base station 300 comprises a housing 305 with a substantially planar base 306 and side walls 307 forming a generally circular shape, though other shapes (triangular, rectangular, oval, etc.) are contemplated herein. The side walls 307 taper from a first height on a first side 302 of the base station 300 to a second height on an opposite side 303 of the base station 300 forming a sloping face 310. Advantageously, the sloping face 310 optimizes the lighted surface so that additional lighted area is viewable by the user to receive visual notifications.

In one aspect, a bottom portion of the housing 305 comprises a circular button 304 coupled to a PCB located within the housing 305. When a user depresses the face 310 of the base station 300, the button or switch 304 is activated. In one aspect of the technology, the button or switch 304 is configured to provide the user with the ability to change settings of the base station 300, including turning the base station 300 on or off. The base station 300 may include a rechargeable battery and/or be powered from an external source.

The face 310 comprises a generally circular void or depression 320 sized to approximate the top portion 211 of the contact enclosure 210. In this manner, the void 320 is configured to receive the top portion 211, including the nose 204, of the contact enclosure 210 therein in order to charge the contact enclosure 210. An inner perimeter of the void 320 comprises a magnet which is intended to help retain the nose 204 of the enclosure 210 within the void 320.

In one aspect of the technology, the face 310 of the base station also comprises a light source coupled to the PCB of the base station 300, the sensor module 200, and/or a remote device. In one aspect of the technology, the base station 300 provides different light and sound notifications for different states sensed by the sensor module 200. In one aspect, the base station will pulse white when the sensor module 200 is charging, will be solid white when fully charged, or bounding white if the sensor module 200 is not pairing with the base station 300. In one aspect, the base station 300 will display bouncing green lights when the base station 300 is attempting to take a reading from the sensor module 200. When the base station 300 is receiving readings from the sensor module 200, it will display pulsing green lights. In one aspect, the base station with flash yellow and play a song (or provide some other audible indicator) indicating that the sock 100 has fallen off or the sensor module 200 is not correctly placed on the infant and was unable to get a reading for a period of time, such as periods of at least 60 seconds, 90 seconds, 120 seconds, etc. During a yellow notification, the base station 300 will send a notification to an application downloaded on a user device (e.g., mobile phone, tablet, etc.) indicating that the sock 100 has fallen off or the sensor module 200 did not get a reading. In another aspect of the technology, the base station 300 will flash blue and play a song (or provide some other audible indicator) indicating that the sensor module 200 is out of range of the base station 300, the battery of the sensor module 200 is depleted, or the signal from the sensor module 200 is blocked for a period of time, such as periods of at least 60, 90, or 120 seconds. In another aspect of the technology, the base station 300 will flash red and emit a high pitched alarm (or other audible notification) indicating that the sensor module 200 has detected a condition requiring the user to check on the infant. In one aspect of the technology, a condition requiring the user to check the infant includes, but is not limited to, an indication that the infant's blood oxygen has dropped below 80% of normal, the infant's heart rate has dropped below 60 beats per minute when the blood oxygen is also below 85%, or the infant's heart rate is greater than 220 beats per minute. Of course, the base station 300 can be configured to provide a red indication at any setting desired, including exceeding temperature thresholds, low heart rates at different blood oxygen levels or temperatures, or the like. In one aspect of the technology, data is sent to an application loaded onto a user's electronic device (mobile phone, tablet, desktop, laptop, etc.). The application displays data related to readings of the infant's (or other user's) heart rate, oxygen, and sleep for a previous period of time (e.g., 5, 10, or 15 minutes, etc.)

The above description provides numerous specific details for a thorough understanding of the embodiments described herein. However, those of skill in the art will recognize that one or more of the specific details may be omitted, or other methods, components, or materials may be used. In some cases, operations are not shown or described in detail. Furthermore, the described features, operations, or characteristics may be combined in any suitable manner in one or more embodiments. It will also be readily understood that the order of the steps or actions described in connection with the embodiments disclosed may be changed as would be apparent to those skilled in the art.

As will be appreciated by one skilled in the art, aspects of the present technology may be embodied as a system, method or used with a computer program product as part of an infant monitoring device. Accordingly, aspects of the present technology may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present technology may take the form of a computer program product embodied in one or more computer readable medium(s) having computer readable program code embodied thereon.

Any combination of one or more computer readable medium(s) may be utilized in recording and reporting the data collected from the device. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, blue tooth, etc., or any suitable combination of the foregoing. Computer program code for carrying out operations for aspects of the present technology may be written in any combination of one or more programming languages, including an object oriented programming language such as Java, Visual Basic, SQL, C++ or the like and conventional procedural programming languages, such as the "C" programming language or similar programming languages. The program code may execute entirely on a user's computer, partly on the user's computer, as a stand-alone software package, partly on the user's computer and partly on a remote computer, entirely or partly within a monitor controller, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The foregoing detailed description describes the technology with reference to specific exemplary embodiments. However, it will be appreciated that various modifications and changes can be made without departing from the scope of the present disclosure. The detailed description and accompanying drawings are to be regarded as merely illustrative, rather than as restrictive, and all such modifications or changes, if any, are intended to fall within the scope of the present disclosure as described and set forth herein.

The invention claimed is:

1. An infant monitoring device, comprising:
   a garment configured to be worn about a portion of a body of an infant, the garment comprising a planar base and a planar strap, wherein the planar base comprises an inner layer and an outer layer, and wherein the planar base is configured to be removably coupled to a sensing module;
   the sensing module comprising fabric enclosure having opposing wings and an electronics sub-assembly comprising opposing wings extending outward from a portion of the electronics sub-assembly, said wings comprising one or more sensors configured to collect information from the infant;
   wherein the opposing wings of the electronics sub-assembly are coupled to the opposing wings of the fabric enclosure; and
   wherein the opposing wings of the fabric enclosure are sized to approximate a void formed in the inner layer so as to at least partially secure the sensing module to the garment.

2. The infant monitoring device of claim 1, wherein the sensing module comprises a charging enclosure covering a circuit board and further housing a battery coupled to the circuit board.

3. The infant monitoring device of claim 2, wherein a portion of the charging enclosure extends through a through-hole in the planar base of the garment.

4. The infant monitoring device of claim 2, wherein the charging enclosure comprises a ridge disposed about the charging enclosure, said ridge defining a top portion of the charging enclosure, the top portion of the charging enclosure being disposed about a first side of the planar base of the garment, a bottom portion of the charging enclosure being disposed about a second, opposite side of the planar base of the garment.

5. The infant monitoring device of claim 2, wherein the fabric enclosure is triangular shaped and is coupled to a portion of the planar base that is triangular shaped.

6. The infant monitoring device of claim 2, wherein the electronics sub-assembly further comprises an antenna configured to receive and transmit data collected by the sensors to a base station.

7. The infant monitoring device of claim 2, wherein the charging enclosure comprises a flexible trace coupled to the circuit board and a spring contact pin pressing against an internal wall of the charging enclosure.

8. The infant monitoring device of claim 2, wherein the sensing module further comprises an attachment plate shaped to approximate a bottom perimeter of the charging enclosure, the attachment plate being coupled to a bottom of the charging enclosure.

9. The infant monitoring device of claim 2, wherein the charging enclosure comprises a charging contact.

10. The infant monitoring device of claim 1, wherein the sensing module comprising the fabric enclosure, electronics sub-assembly, and sensors is formed into a single unit.

11. An infant monitoring device and base station, comprising:
    a garment configured to be worn about a portion of a body of the infant, the garment comprising a base, wherein the base is configured to be removably coupled to a sensing module;
    the sensing module comprising fabric enclosure, wherein the base comprises a void sized to approximate opposing wings formed on the fabric enclosure, the void configured to at least partially secure the sensing module to the garment;
    the fabric enclosure housing an electronics sub-assembly having sensors configured to collect information from the infant, wherein a portion of the electronics sub-assembly is housed within a charging enclosure, the charging enclosure coupleable to a base station;
    the base station comprising a housing having a planar base and sidewalls, the sidewalls tapering from a first height on a first side of the base station to a second height on a second opposite side of the base station forming a sloping top face.

12. The monitoring device and base station of claim 11, wherein the sloping face comprises a depression shaped to approximate a top portion of the charging enclosure.

13. The monitoring device and base station of claim 11, wherein the base station comprises a light source coupled to a power source and a circuit board.

14. The monitoring device and base station of claim 13, wherein the base station comprises an antenna configured to transmit and receive data collected by the sensing module.

* * * * *